United States Patent [19]

Kremer et al.

[11] 4,411,524
[45] Oct. 25, 1983

[54] APPARATUS FOR THE SPECTROMETRIC ANALYSIS OF THE CHEMICAL COMPOSITION OF METALLIC PARTS

[75] Inventors: Karl J. Kremer; Jochen Brauner, both of Siegen; Klaus-Dieter Glaubitz, Hilchenbach; Helmut Eckstein; Josef Bruggemann, both of Wenden, all of Fed. Rep. of Germany

[73] Assignee: Krup Stahl, A.G., Bochum, Fed. Rep. of Germany

[21] Appl. No.: 273,681

[22] Filed: Jun. 15, 1981

[30] Foreign Application Priority Data

Jul. 31, 1980 [DE] Fed. Rep. of Germany ....... 3029038

[51] Int. Cl.³ .............................................. G01N 21/67
[52] U.S. Cl. .................................................... 356/313
[58] Field of Search ......................................... 356/313

[56] References Cited

U.S. PATENT DOCUMENTS 3,909,133 9/1975 Hobson et al. ...................... 356/313
3,942,892 3/1976 Ambrose et al. .................... 356/313
4,037,962 7/1977 Grisar et al. ......................... 356/313

FOREIGN PATENT DOCUMENTS 1574032 9/1980 United Kingdom ............... 356/313

Primary Examiner—F. L. Evans
Attorney, Agent, or Firm—Morse, Altman & Dacey

[57] ABSTRACT

An apparatus for the spectrometric analysis of the chemical composition of metallic parts comprising a probe designed to be placed on the part and having a device for vaporizing the part. Means is provided for spacing the device from the part and also means for sensing the radiation emitted by the part vaporized by the device. A protective gas preferably continuously is admitted into the vicinity of the device and of the sensing means. Preferably, the probe is portable, hand-held, and enables outdoors the rapid determination of metals, particularly their carbon content, including those whose wavelength region is below 250 nm.

9 Claims, 5 Drawing Figures (A)

APPARATUS FOR THE SPECTROMETRIC ANALYSIS OF THE CHEMICAL COMPOSITION OF METALLIC PARTS

BACKGROUND OF THE INVENTION

1. Field of the Invention

The present invention relates generally to spectrometers and, more particularly to an apparatus for the rapid determination of metals in the outdoors.

2. The Prior Arts

Apparatus for the spectrometric analysis of the chemical composition of substances, such as metallic parts, have been known for some time. In a known apparatus of this type, two or three spacing supports are located adjacent a vaporizing device, formed as a spark electrode, and holding the spark electrode at a definite distance from the substance when positioned on the substance. The radiation emitted by the metal vapor brought to luminescence by the device is transferred to a spectroscope by a flexible optical waveguide. The waveguide is fastened to the base of a probe and its free end constitutes the sensing head and is pointed towards the plasma of the luminous metal vapor. The spectroscope is housed in a mobile unit, which also contains the energy source for the vaporizing device (German Pat. No. 2,626,233).

It has been learned that external factors affect the operation and the range of application of such an apparatus. Specifically, factors which impair the stability of a plasma, such as the stability of a spark or of an arc, and factors which affect the transmission of the radiation from the luminous metal vapor to the sensing head. Thus, the stability of the spark is impaired by uncontrollable air currents which can not be completely eliminated by the location of the spark electrode in a chamber alone. The transmission of the radiation is attenuated when passing through air. The attenuation depends on the wavelength of the light and increases as the wavelength becomes shorter. This known manually-operated apparatus is accordingly suitable only for the determination of components with long wavelengths. The analytical determination of components which produce radiation of short wavelengths must, therefore, be accomplished in a laboratory with stationary equipment, now as in the past. In the laboratory, a sample of the part to be analyzed is studied in a protective gas atmosphere, such as an argon atmosphere, whereby wavelengths below 250 nm can also be determined.

Another disadvantage of this known equipment resides in that that part of the vaporized material itself settles on the sensing head which weakens the transmitted radiation. The apparatus, therefore, must be cleaned from time to time.

Besides apparatus of this kind, equipment is known in which the spectrometric analytical apparatus is accommodated in a portable cabinet, housing the vaporizing device. A sleevelike chamber, open on one end, surrounds the device and serves as a spacing support. This apparatus is unwieldy and requires great physical effort for handling by an operator (German Pat. Nos. 2,513,345 and 2,513,358).

A device is also known in which an opening is provided in the rear of the electrode chamber through which gases formed are allowed to escape (British Pat. No. 1,444,255).

SUMMARY OF THE INVENTION

It is a principal object of the present invention to overcome the above disadvantages by providing an improved portable apparatus for the rapid determination of metallic parts in the outdoors.

More specifically, it is an object of the present invention to provide an apparatus for the spectrometric analysis of the chemical composition of metallic parts characterized by improved stability in its spark, by an expanded range of use, and by a greater freedom from maintenance. The apparatus of the invention comprises a probe designed to be placed on the metallic part and having a device for vaporizing the part, means for spacing the device from the part, means for sensing the radiation emitted by the part vaporized by the device, and means for continuously admitting a protective gas into the vicinity of the device and of the sensing means so as to continuously flushing the same. Preferably, the protective gas is argon. The gas enables the sensing of short-wave radiation by the sensing means, particularly that of carbon, in the wavelength region below 250 nm. Preferably, the means for spacing the vaporizing device from the part comprises a chamber containing the device and whose open end is designed to be placed on the part, a window formed in the chamber, with the sensing means positioned adjacent the window, and a tubular member communicating with the chamber for admitting the gas therein. Preferably, the gas is admitted into the chamber on a side of the vaporizing device opposite to the window. Preferably, the tubular member communicates with the chamber at a location farther from its open end than is the location of the window. Preferably, the size of the tubular member is smaller than the size of the window so as to provide a smooth and uniform flushing of the chamber, with a gentle flow past the sensing means. Preferably, the open end of the chamber designed to be placed on the metal part is provided with a plurality of serrations, effecting good electrical contact therewith.

Preferably, the apparatus includes a number of nozzles, preferably ringlike, arranged about the outside of the chamber to direct a coolant at the chamber. Preferably, the vaporizing device is supported by a heat sink provided with cooling means. Preferably, the cooling means is a fan. Further stabilization of the spark is achieved by providing a screen, preferably formed of boron nitride, and positioned within the chamber between its open end and the vaporizing device. The screen facilitates controlled flushing of the surface of the metal part with the protective gas.

Other and further objects of the present invention will in part be obvious and will in part appear hereinafter.

The invention accordingly comprises a spectrometric apparatus of the present disclosure, its components, parts and their interrelationships, the scope of which will be indicated in the appended claims.

BRIEF DESCRIPTION OF THE DRAWINGS

For fuller understanding of the nature and objects of the present invention, reference is to be made to the following detailed description, which is to be taken in connection with the accompanying drawings, wherein.

Figure 1:
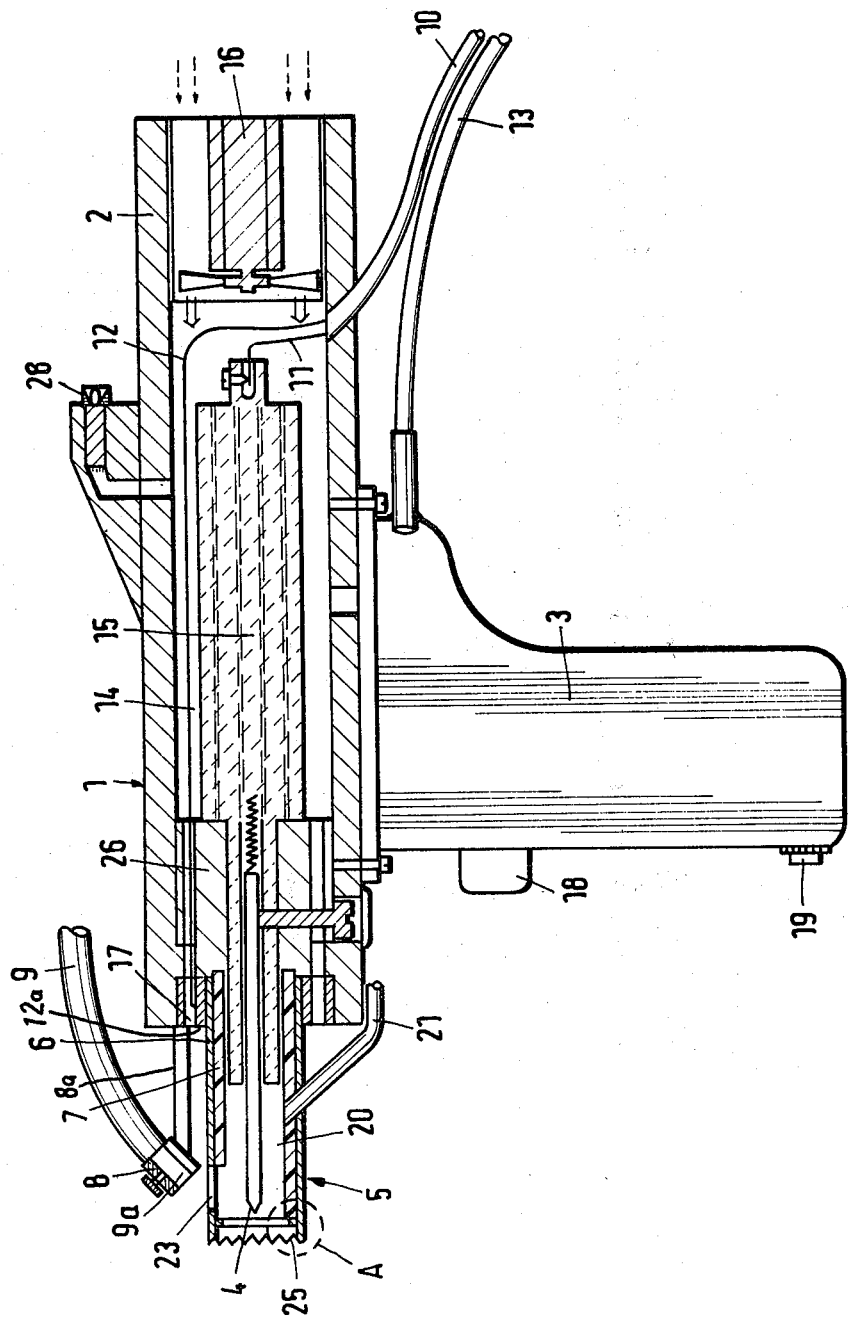
FIG. 1 is a view, in side elevation and partly in axial section, of a probe constructed in accordance with the present invention.
Figure 2:
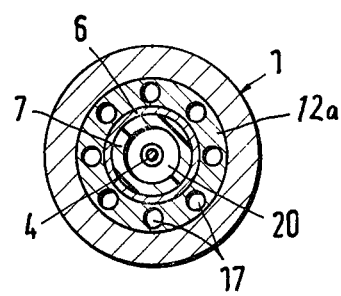
FIG. 2 is a cross section of the front portion of the probe of FIG. 1, but on an enlarged scale.
Figure 3:
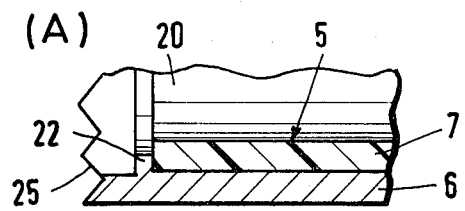
FIG. 3 is a fragmentary axial section, on an enlarged scale, of the open front portion of the probe of FIG. 1.
Figure 4:
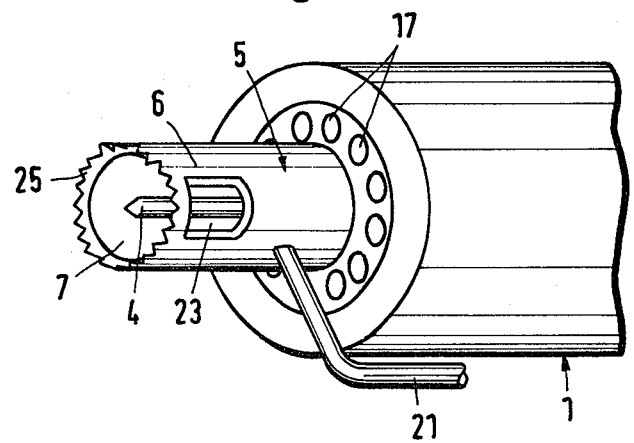
FIG. 4 is a perspective view, on an enlarged scale, of the front portion of the probe of FIG. 1.
Figure 5:
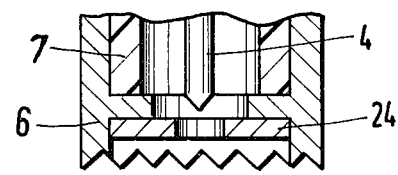
FIG. 5 is a fragmentary axial section, on an enlarged scale, of the front portion of the probe shown in FIG. 1.

The apparatus for the spectrometric analysis of the chemical composition of metallic parts constructed in accordance with the invention essentially comprises a probe 1, shown in side elevation and partly in axial section in FIG. 1. As may be noted, the probe 1 is constructed with an exterior shape of a pistol and includes a housing 2 and a handle 3. The probe 1 is connected via flexible cables yet to be described to a unit, not shown. This unit includes a spectrometric analysis apparatus, a power source, electronic control devices, and a source of protective gas.

The housing 2 supports, at its forward end, a vaporizing device such as a spark electrode 4. The spark electrode 4 is surrounded concentrically by an annular chamber 5 formed with an electrically conductive outer wall 6 provided with an insulating sleeve 7. The outer wall 6 also is supported, preferably concentrically, within the tubular housing 2. The spark electrode 4 is connected electrically to a lead 11 of a flexible cable 10 leading to the power source in the unit, not shown. The electrically conductive outer wall 6 in turn is connected to a lead 12 of the cable 10. The electrical connection between the lead 11 and the spark electrode 4 preferably is effected through a heat sink 15, in which the electrode 4 is firmly clamped, coaxially with respect to the tubular housing 2. The lead 12 is disposed in an annular space 14 formed between the heat sink 15 and the housing 2. The lead 12 is connected directly to an annular disc 12a, conductively surrounding the outer wall 6 and concentrically secured therebetween and the housing 2. The annular disc 12a is provided with a plurality of nozzles 17 circumferentially, i.e., ringlike disposed about the outer wall 6 of the chamber 5. An insulating member 26 supports the heat sink 15 concentrically within and spaced from the wall of the housing 2. The insulating member 26 is provided with a plurality of apertures aligned with and corresponding to the plurality of circumferential nozzles 17 formed in the annular disc 12a.

The rear portion of the chamber 5 is provided with an opening for a tube 21. A suitable protective gas, such as argon, preferably is continuously admitted into the interior 20 of the chamber 5 via the tube 21. In the vicinity of the front open end of the chamber 5 is a window 23. The protective gas admitted into the chamber 5 via the tube 21 is permitted to escape from the interior 2o thereof through the window 23. A sensor head 9a of an optical waveguide cable 9 is mounted directly adjacent the window 23 on the outside of chamber 5. The sensor head 9a is supported at a slight angle to the longitudinal axis of the housing 2 by a suitable sleevelike holder 8, which in turn is secured to the housing 2 via a supporting member 8a. The sensor head 9a is facing toward the window 23 so that it can receive radiation emanating from the window 23. The sensor head 9a is tilted at the noted slight angle so that its face be positioned in the stream of the protective gas continuously leaving the interior 2o of the chamber 5 through the window 23, which stream protects the sensor head 9a against the deposit of vaporized material. Preferably, the tube 21 and the optical waveguide cable 9 are flexible, and are respectively connected to the spectrometer and to the source of the protective gas in the unit, not shown.

The front edge of the probe 1, represented by the front end of the conductive outer wall 6 of the chamber 5, preferably is formed with a plurality of serrations 25. When the probe 1 is positioned with its front end on the surface of a metallic part, the protective gas continuously being admitted into the chamber 5 via the tube 21 is also permitted to escape through this serrated end so as to flush the metal's surface. Preferably, a screen 24, formed of boron nitride, also is disposed in the front portion of the chamber 5. The screen 24 is shown supported on an annular shoulder 22, between the serrated end 25 and the end of the spark electrode 4.

A fan 16 preferably is located in the distal end of the housing 2, opposite to the chamber 5. The fan 16 is designed to direct a coolant medium, such as air, against the heat sink 15 and, via the annular space 14, to and through the circumferential nozzles 17. The coolant medium exiting through the nozzles 17 is intended to impinge upon the conductive outer wall 6 of the chamber 5.

The probe 1 is connected, via a flexible control cable 13, to the appropriate control parts of the unit, not shown. The control and guidance of the probe 1 is effected via the handle 3, being hand-held, and a starter switch 18 disposed on the handle 3. Electric power from the energy supply in the unit is turned on by depressing the starter switch 18. After completion of one measurement cycle, the probe 1 is reset for a new measurement via a reset switch 19, also disposed on the handle 3. A control display 28 mounted on the housing 2 visually indicates to the operator whether or not the measurement just made meets the predetermined desired criteria.

The apparatus constructed according to the invention is favorably characterized by its ease of handling, since the operator needs to handle only the light-weight probe 1 connected via flexible cables to the heavier unit. The continously admitted protective gas effects a constant flushing of the chamber 5 and all around the sensor head 9a of the quartz optical waveguide cable 9. As a consequence, the radiation path to the sensor head 9a is kept clear of any potentially interferring layers of air. Further, any undesirable deposition of vaporized metal on the sensor head 9a is avoided. Otherwise, such deposition of vaporized metal on the sensor head 9a would adversely affect radiation measurements by the probe 1. Continuously filling and flushing of the chamber 5 makes it possible effectively to use the probe 1 outdoors, since the protective gas protects the sparks from the spark electrode 4 from air currents.

Thus it has been shown and described an improved apparatus designed for the spectrometric analysis of metallic parts, which apparatus satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. Apparatus for the spectrometric analysis of the chemical composition of metallic parts comprising a probe designed to be placed on the metallic part, said probe having a device for vaporizing said part, means for spacing said device from said part, and means for sensing the radiation of metallic vapor brought to luminescence by said vaporizing device, characterized in that, said means for spacing said device from said part comprises a chamber containing said device and provided with an open end;

said vaporizing device being a spark electrode coupled to a power source and said chamber as contact bridge for transferring the current of said power source;

said open end of said chamber designed to be placed on said part and provided with a plurality of serrations;

a window formed in said chamber, with said sensing means positioned adjacent said window and on the outside of said chamber;

a tubular member communicating with said chamber for admitting a protective gas into said chamber; and a number of nozzles arranged about the outside of said chamber to direct a coolant thereat.

2. The apparatus of claim 1 wherein said tubular member communicates with said chamber at a side of said vaporizing device opposite said window.

3. The apparatus of claim 1 wherein said tubular member communicates with said chamber farther away from its said open end then said window, particularly the rear edge of said window.

4. The apparatus of claim 1 wherein the distance separating said sensing means from said window is less than the height of said window.

5. The apparatus of claim 1 wherein the free space sectional area of said tubular member communicating with said chamber is smaller than the free-space opening of said window.

6. The apparatus of claim 1 wherein said nozzles surround said chamber ringlike.

7. The apparatus of claim 1 wherein said vaporizing device is supported by a heat sink and further including cooling means for said heat sink.

8. The apparatus of claim 7 wherein said cooling means is a fan.

9. The apparatus of claim 1 further including a screen formed of boron nitride and positioned within said chamber between said open end thereof and said vaporizing device.

* * * * *